(12) United States Patent
Moriarty et al.

(10) Patent No.: US 6,358,746 B1
(45) Date of Patent: Mar. 19, 2002

(54) FLUORESCENT COMPOUNDS FOR USE IN INDUSTRIAL WATER SYSTEMS

(75) Inventors: Barbara E. Moriarty, Palatine, IL (US); Jerry L. Reddinger, Austin, TX (US)

(73) Assignee: Nalco Chemical Company, Naperville, IL (US)

( * ) Notice: Subject to any disclaimer, the term of this patent is extended or adjusted under 35 U.S.C. 154(b) by 0 days.

(21) Appl. No.: 09/436,189

(22) Filed: Nov. 8, 1999

(51) Int. Cl.$^7$ ................................................. G01N 37/00
(52) U.S. Cl. ............................... 436/56; 436/55; 422/3; 422/16; 422/62; 546/100; 544/126; 544/331; 544/332; 544/333; 544/361
(58) Field of Search ....................... 436/55, 56; 422/62, 422/3, 16; 546/100; 544/126, 331, 332, 333, 361

(56) References Cited

U.S. PATENT DOCUMENTS

| | | | |
|---|---|---|---|
| 4,079,001 A | * 3/1978 | Haase et al. | 210/36 |
| 4,172,202 A | * 10/1979 | Papehfuhs | 546/100 |
| 4,783,314 A | 11/1988 | Hoots et al. | |
| 4,992,380 A | 2/1991 | Moriarty et al. | |
| 5,006,311 A | 4/1991 | Hoots et al. | |
| 5,389,548 A | 2/1995 | Hoots et al. | |
| 5,411,889 A | 5/1995 | Hoots et al. | |
| 5,705,394 A | * 1/1998 | Ananthasubramanian et al. | 436/55 |
| 5,958,788 A | * 9/1999 | Johnson et al. | 436/172 |

FOREIGN PATENT DOCUMENTS

EP 0 640 747 B1 3/1997

* cited by examiner

*Primary Examiner*—Jill Warden
*Assistant Examiner*—Monique T. Cole
(74) *Attorney, Agent, or Firm*—Margaret M. Brumm; Thomas M. Breininger

(57) ABSTRACT

Fluorescent compounds of the formula:

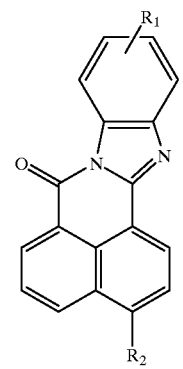

wherein $R_1$ and $R_2$ are either both $SO_3M$, or one of $R_1$ and $R_2$ is $SO_3M$ and the other is COOM, where M is selected from the group consisting of H, Na, K, Rb, Cs, Li or ammonium, are described and claimed. These inert flurorescent compounds have been found to be resistant to oxidizing biocides. One process for making these compounds is described and claimed as the condensation between a 1,8-naphthalic anhydride possessing the desired functionalities and the appropriately substituted o-phenylene diamine. Alternatively, o-amino-nitro-aromatics may be condensed with the various 1,8-naphthalic anhydrides when the in situ reduction of the nitro group is accomplished with a suitable reducing agent such as iron powder. The resulting fluorescent compounds can be used as inert fluorescent tracers in industrial water systems.

16 Claims, No Drawings

FLUORESCENT COMPOUNDS FOR USE IN INDUSTRIAL WATER SYSTEMS

FIELD OF THE INVENTION

This invention relates to fluorescent compounds. In one aspect it relates to fluorescent compounds that have been synthesized and undergone stability testing for use as inert tracers in industrial water systems. In another aspect of this invention there are provided alternative processes for the production of fluorescent compounds.

BACKGROUND OF THE INVENTION

Using an inert fluorescent compound to track the hydraulic losses and gains from an industrial water system has been known since the late 1980's.

Industrial water systems are very numerous. One typical industrial water system is a cooling tower where water is used in a heat exchange role. To optimize use of treating agents in such systems and to assure overall appropriate hydraulic conditions are maintained in the system, it is advantageous to determine the amount of treating agent added to the system in accordance with recommended use levels specific to the environment. If there is an under treatment of treating agent, deposition of scaling salts and corrosion may rapidly occur. If there is an over treatment of treating agent, treating agent will be wasted with a commensurate loss of money.

The continuous on-stream monitoring of the amount of a treating agent added to a moving body of water through the use of a tracer comprising an inert fluorescent compound is an established practice as described in U.S. Pat. Nos. 4,783,314 and 4,992,380. These patents contain background information which need not be repeated here but the contents of which are incorporated herein by reference.

To be useful in such systems, the fluorescent compound employed must be non-consumable or system-inert. There are certain known compounds that are capable of functioning as inert fluorescent tracers, however, there are not an abundance of such compounds. Therefore, there is a continuous need for the development of additional inert fluorescent tracer compounds that are capable of functioning in aqueous systems, particularly where such systems contain oxidizing biocides.

SUMMARY OF THE INVENTION

The first aspect of the instant claimed invention is a fluorescent compound of the formula:

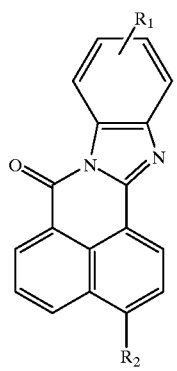

I wherein $R_1$ and $R_2$ are either both $SO_3M$, or one of $R_1$ and $R_2$ is $SO_3M$ and the other is $COOM$, where M is selected from the group consisting of H, Na, K, Rb, Cs, Li or ammonium.

The second aspect of the instant claimed invention is a process for the preparation of a fluorescent compound having the formula:

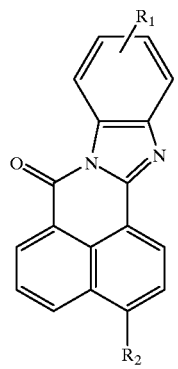

I wherein $R_1$ and $R_2$ are as defined previously, which comprises condensing a 1,8-naphthalic anhydride of the formula:

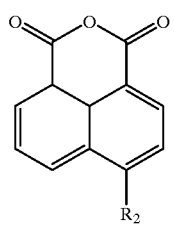

II with an o-phenylene diamine of the formula:

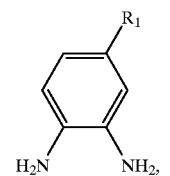

III where $R_1$ and $R_2$ are as defined previously.

The third aspect of the instant claimed invention is a process to make fluorescent compounds of formula I:

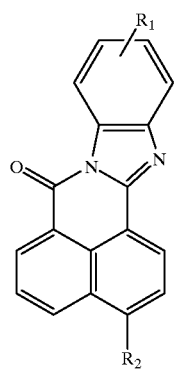

I by condensing o-amino-nitro aromatics of the formula

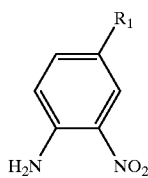

IV where $R_1$ is as defined previously, with the appropriate 1,8-naphthalic anhydride:

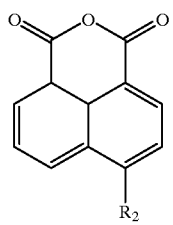

II where $R_2$ is as defined previously,
wherein such condensation is carried out in such a manner that in situ reduction of the nitro group is accomplished with a suitable reducing agent.

The fourth aspect of the instant claimed invention is the use of a compound of formula:

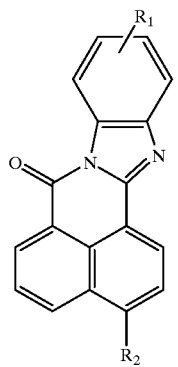

I where $R_1$ and $R_2$ are as defined previously, as an inert fluorescent tracer in an industrial water system.

DETAILED DESCRIPTION OF THE INVENTION

This invention is based upon the discovery of certain naphthalimide-based compounds. These naphthalimide-based compounds are not only fluorescent, but are also stable in the presence of oxidizing biocides such as bleach, bromine, stabilized chlorine and stabilized bromine. Therefore, these certain naphthalimide-based compounds are particularly useful as inert fluorescent tracers in industrial water systems containing bleach and/or stabilized bromine.

These certain naphthalimide-based compounds can be readily prepared through the condensation between a 1,8-naphthalic anhydride possessing the appropriate functionalities with the appropriately substituted o-phenylene diamine. They can also be prepared by the condensation of a 1,8-naphthalic anhydride possessing the appropriate functionalities with an o-amino-nitro aromatic in the presence of a suitable reducing agent.

The fluorescent compounds of the present invention are naphthalimide-based compounds of the following structure:

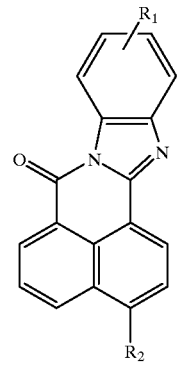

I wherein $R_1$ and $R_2$ are either both $SO_3M$, or one of $R_1$ and $R_2$ is $SO_3M$ and the other is COOM, where M is selected from the group consisting of H, Na, K, Rb, Cs, Li or ammonium.

The fluorescent compounds of the present invention can be conveniently prepared by a one-step condensation between a 1,8-naphthalic anhydride possessing the desired functionalities and the appropriately substituted o-phenylene diamine. Suitable 1,8-naphthalic anhydrides for preparing the fluorescent compounds in accordance with the present invention are ones selected from the group of the formula:

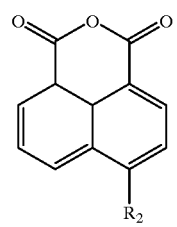

II wherein $R_2$ is as defined previously. When $R_2$ is $SO_3K$, then Compound II is 4-sulfo-1,8-naphthalic anhydride, potassium salt and Compound II is available from Aldrich Chemical Company, P.O. Box 2060, Milwaukee, Wis. 53201 USA; Telephone Numbers (414) 273-3850 and (800) 558-9160.

Similarly suitable o-phenylene diamine compounds which are useful in the preparation of the fluorescent compounds of the present invention are ones of the formula:

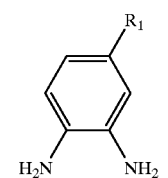

III wherein $R_1$ is as defined previously. When $R_1$ is COOH, then Compound III is 3,4-diaminobenzoic acid and Compound III is available from Aldrich. When $R_1$ is $SO_3H$, then Compound III is 3,4-diaminobenzene sulfonic acid and Compound III is available from Bayer AG, Organic Chemicals Business Group, Marketing, Leverkusen, D-51368, Germany, Telephone Number +49 214 30-8514.

In a presently preferred embodiment of this invention, the fluorescent compounds can be prepared in a one-step condensation between an appropriately substituted naphthalic anhydride and an appropriately substituted o-phenylene diamine.

Alternatively, o-amino-nitro aromatics of the formula

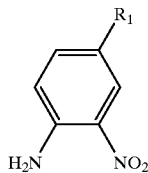

IV where $R_1$ is as defined previously, can be condensed with the appropriate 1,8-naphthalic anhydride when such condensation is carried out in such a manner that in situ reduction of the nitro group is accomplished with a suitable reducing agent such as, but not limited to, iron powder. When $R_1$ is $SO_3M$ then compound IV is o-nitroaniline-p-sulfonic acid (and salts thereof) and Compound IV is available from Bayer AG. When $R_1$ is CO OH, then Compound IV is 4-amino-3-nitro benzoic acid, and Compound IV is available from ACROS Organics, which is part of Fisher Scientific, 600 Business Center Drive, Pittsburgh Pa. 15205, telephone number 1-800-227-6701. When $R_1$ is $SO_3M$ then Compound IV is 2-nitroaniline-4-sulfonic acid and its salts, and Compound IV is available from TCI America, 9211 North Harborgate Street, Portland Oreg. 97203, telephone number 800-423-8616.

Fluorescence is defined as the reemission of longer wavelength (lower frequency) photons (energy) by a molecule that has absorbed photons (light) of shorter wavelengths (higher frequency). Both absorption and radiation (emission) of energy are unique characteristics of a particular molecule (structure) during the fluorescence process. Light is absorbed by molecules causing electrons to become excited to a higher electronic state. The electrons remain in the excited state for about $10^{-8}$ second then, assuming all of the excess energy is not lost by collisions with other molecules, the electron returns to the ground state. Energy is emitted during the electrons' return to their ground state. The Stokes' shift is the difference in wavelength between absorbed and emitted light. The emitted wavelength is always longer or equal to the incident wavelength, due to energy conservation; the difference is absorbed as heat in the atomic lattice of the material.

When their fluorescent properties were tested, it was found that the instant claimed compounds have a fluorescent signal excitation value above 380 nm. Thus, these compounds have a different fluorescent signal than Nalco Chemical Company's inert tracer 1,3,6,8-pyrene tetrasulfonic acid tetrasodium salt (PTSA). PTSA is available from Nalco Chemical Company, One Nalco Center, Naperville, Ill. 60563, telephone number (630) 305-1000. Thus, the instant claimed tracers can be used together with PTSA for monitoring and control purposes in an industrial water system, because their fluorescent signal does not overlap with that of PTSA.

The inert fluorescent compounds of this invention exhibit excitation and emission maxima in the range of 385–400 nm and 510–530 nm respectively. This broad spectral operating range, afforded by the compounds of the present invention, will enhance the utility of these compounds as inert fluorescent tracers. In addition, the large difference between the excitation and emission maxima (called the Stokes shift) may serve to minimize interference due to background hydrocarbons, since very few species have a Stokes shift this large.

The fluorescent compounds of this invention can be used in any industrial water system where an inert fluorescent tracer is needed. Examples of such systems are cooling tower water systems (including open recirculating, closed and once-through systems); petroleum wells, downhole formations, geothermal wells and other oil field applications; boilers and boiler water systems; mineral process waters including mineral washing, flotation and benefaction; paper mill digesters, washers, bleach plants and white water systems; black liquor evaporators in the pulp industry; gas scrubbers and air washers; continuous casting processes in the metallurgical industry; air conditioning and refrigeration systems; industrial and petroleum process water; indirect contact cooling and heating water, such as pasteurization water; water reclamation and purification systems; membrane filtration water systems; food processing streams (meat, vegetable, sugar beets, sugar cane, grain, poultry, fruit and soybean); and waste treatment systems as well as in clarifiers, liquid-solid applications, municipal sewage treatment and industrial or municipal water systems.

When using the fluorescent compounds of this invention as inert tracers in industrial water systems, it is generally desirable to employ the least amount of fluorescent compound that is practical for the circumstances. It is, of course, understood that the amount of the fluorescent compound added to the water system has to be at least an amount sufficient for the fluorescent signal measurements to be made. Generally, the system concentration of an insert fluorescent compound at the sampling site in the water system should be at least about 0.01 ppb and not more than about 10 ppm. Preferably the concentration of fluorescent compound is between about 50 ppb and about 500 ppb. Most preferably the concentration of fluorescent compound is between about 100 ppb and 400 ppb. Of course, it is possible to add more than 10 ppm of the inert fluorescent compound to the water system and detect the fluorescent signal of the compound, but the use of any amount of inert fluorescent compound over 10 ppm is an unnecessary waste of inert fluorescent compound.

The meaning of the term "inert", as used herein is that an inert fluorescent tracer is not appreciably or significantly affected by any other chemistry in the system, or by the other system parameters such as metallurgical composition, microbiological activity, biocide concentration, heat changes or overall heat content. To quantify what is meant by "not appreciably or significantly affected", this statement means that an inert fluorescent compound has no more than a 10% change in its fluorescent signal, under conditions normally encountered in industrial water systems. Conditions normally encountered in industrial water systems are known to people of ordinary skill in the art of industrial water systems.

Of course it is possible to cause more than a 10% change in the fluorescent signal by subjecting the fluorescent compound to stress that is not normal for an industrial water system. For example, the fluorescent signal of one of the instant claimed compounds (disulphonaphthalimide or DSN) will change more than 10% if the compound encounters more than 42000 ppm of pyrophosphate (as $PO_4$), or if it encounters more than 34000 ppm of sodium (as $Na^+$). The fluorescent signal of another one of the instant claimed compounds (carboxysulpho naphthalimide or CSN) will change more than 10% if the compound encounters more than 3100 ppm of silicates (as $SiO_2$), or if it encounters more than 41000 ppm of sodium (as $Na^+$).

The instant claimed compounds have been found to remain inert when encountering the standard components of industrial water systems. However, it has also been found that the inertness of the instant claimed compounds can be challenged by a change in pH. The DSN compound has been found to be inert over a pH range of from about 2 to about 9 and the CSN compound has been found to be inert over a pH range of from about 5 to about 10. When operating the water system within these pH ranges it has been found that both DSN and CSN are effective inert fluorescent tracers.

An advantage provided by the fluorescent compounds of this invention is that they have been found to be inert to the degradation effects of oxidizing biocides. Therefore, they are particularly useful in systems using oxidizing biocide(s) to minimize microbial activity.

EXAMPLES

The following examples are intended to be illustrative of the present invention and to teach one of ordinary skill in the art to make and use the invention. These examples are not intended to limit the invention in any way.

Example I

Preparation of Disulpho Naphthalimide (DSN)

Where $R_1$ is $SO_3Na$ and $R_2$ is $SO_3K$

A 100 ml round-bottomed flask was charged with 3.16 parts of 4-sulfo-1,8-naphthalic anhydride, potassium salt; 2.40 parts of 3-nitro-4-aminobenzenesulfonic acid, sodium salt; 1 part of iron powder, and 30 parts of glacial acetic acid. The mixture was refluxed with vigorous stirring for 6 hours. Upon cooling, the orangish/yellow solid was collected by filtration, washed with deionized water and isopropanol, and dried in vacuo to give 4.21 parts of the title compound. This material was further purified by stirring 4 parts of the crude solid in 100 parts boiling methanol and filtering the hot suspension. Accordingly, 3.65 parts of a dark yellow compound were obtained upon drying in vacuo.

Example II

Preparation of Carboxysulpho Naphthalimide (CSN)

Where $R_1$ is COOH (converted to COOK by using potassium carbonate), and $R_2$ is $SO_3K$ A 100 ml round-bottomed flask was charged with 3.16 parts of 4-sulfo-1,8-naphthalic anhydride, potassium salt; 1.55 parts of 3,4-diaminobenzoic acid, and 30 parts of glacial acetic acid. The mixture was refluxed with vigorous stirring for 6 hours; whereby, the appearance of the suspension changed from a tan color to that of a dull yellow. Upon cooling, the yellow solid was collected by filtration, washed with deionized water, and dried in vacuo to give 4.10 parts of the title compound.

An aqueous solution of CSN can be made by taking 1 part of the title compound, suspending it in 100 parts of deionized water, and rendering the pH of the solution slightly alkaline via the addition of potassium carbonate.

Example III

Oxidizing Biocide Stability of the compounds of Formula I

The oxidizing biocide stability test was performed in the following manner. Solutions of simulated water were prepared with the desired levels of cations and anions at the desired pH. For these experiments the simulated cooling water contained 360 ppm Ca (as $CaCO_3$), 200 ppm Mg (as $CaCO_3$), 300 ppm alkalinity (as $CaCO_3$) and 15 ppm of a phosphonate to prevent $CaCO_3$ precipitation. The water was then adjusted to the desired pH with HCl or NaOH. Tests were performed at pH 9.

A series of three amber bottles were labeled with the desired test sample. 25 ml of the simulated water was delivered into each of the three labeled bottles. To one of the bottles (labeled B) was delivered 30 μL of a 1200-ppm stock solution of bleach. To a second bottle (labeled S) was delivered 30 μL of a 1200 ppm stock solution of a liquid stabilized bromine solution available as STA-BR-EX™ from Nalco Chemical Company. To the third bottle (labeled N) was delivered 30 μL distilled water.

The amount of free and total chlorine was measured immediately after the samples were prepared and 24 hrs. later at the time of fluorescence analysis. The bottles were stored for 24 hrs. in the dark. After 24 hours, fluorescence measurements were done using the sample marked N as the reference sample. The % fluorescence consumed in the presence of an oxidizing biocide was calculated as shown below.

% Fluorescence Consumed =

$$\frac{\text{Intensity of } N \text{ Sample} - \text{Intensity of } B \text{ or } S \text{ Sample}}{\text{Intensity of } N \text{ Sample}} \times 100$$

Oxidizing biocide stability data is presented in Table I. For comparison, known inert fluorescent tracers: 1-methoxypyrene-3,6,8-trisulfonic acid, trisodium salt (available from Molecular Probes, 4849 Pitchford Avenue, Eugene, Oreg. 97402, telephone number (541) 465-8300) and pyrene-1,3,6,8-tetrasulfonic acid tetrasodium salt (PTSA) were included.

TABLE I

Oxidizing Biocide Stability Data for Naphthalimides

| Compound | Excitation (nm) | Emission (nm) | % Consumed in Presence of 1 ppm bleach (as $Cl_2$) over 24 Hrs. | % Consumed in Presence of 1 ppm stabilized Br (as $Cl_2$) over 24 Hrs. |
|---|---|---|---|---|
| The compound of Example I Disulpho naphthalimide | 387 | 510 | 0% | 0% |
| The compound of Example II Carboxysulpho naphthalimide | 398 | 519 | 0% | 3% |
| 1-Methoxypyrene-3,6,8-trisulfonic acid, trisodium salt Comparative Example | 404 | 430 | 12% | 2% |
| 1,3,6,8-pyrenetetra-sulfonic acid, tetrasodium salt Comparative Example | 365 | 400 | 0% | 0% |

In reading the data in the table, the lower the amount (% consumed) of fluorescence consumed, the better.

The results indicate that the compounds of the present invention are stable in the presence of oxidizing biocides, at concentrations typical of cooling water systems. Therefore, they have great utility as tracers in cooling water systems. Further, apart from the inert fluorescent compounds of this invention no other compounds are known that exhibit an excitation above 380 nm which are also stable in the presence of oxidizing biocides.

The specific examples herein disclosed are to be considered as being primarily illustrative. Various changes beyond those described will, no doubt, occur to those skilled in the art; and such changes are to be understood as forming a part of this invention insofar as they fall within the spirit and scope of the appended claims.

That which is claimed is:

1. A fluorescent compound of the formula:

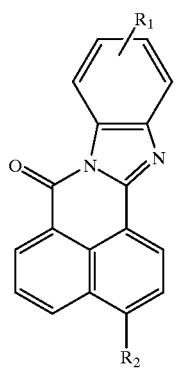

I wherein $R_1$ and $R_2$ are either both $SO_3M$, or one of $R_1$ and $R_2$ is $SO_3M$ and the other is COOM, where M is selected from the group consisting of H, Na, K, Rb, Cs, Li or ammonium.

2. A process for the preparation of a fluorescent compound having the formula of:

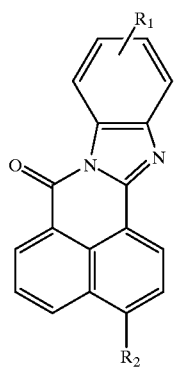

I wherein $R_1$ and $R_2$ are either both $SO_3M$, or one of $R_1$ and $R_2$ is $SO_3M$ and the other is COOM, where M is selected from the group consisting of H, Na, K, Rb, Cs, Li or ammonium, which comprises condensing a 1,8-naphthalic anhydride of the formula:

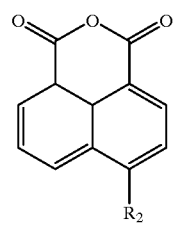

II with an o-phenylene diamine of the formula:

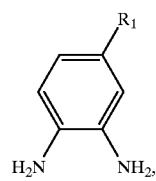

III where $R_1$ and $R_2$ are as defined previously.

3. A process to make compounds of formula I:

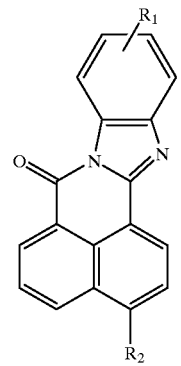

I wherein $R_1$ and $R_2$ are either both $SO_3M$, or one of $R_1$ and $R_2$ is $SO_3M$ and the other is COOM, where M is selected from the group consisting of H, Na, K, Rb, Cs, Li or ammonium, by condensing, o-amino-nitro aromatics of the formula

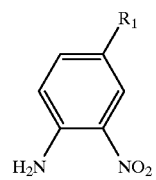

IV where $R_1$ is as defined previously, with the appropriate 1,8-naphthalic anhydride

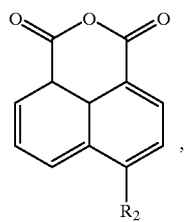

II wherein R$_2$ is as previously defined, wherein such condensation is carried out in such a manner that in situ reduction of the nitro group is accomplished with a suitable reducing agent.

4. The compound of claim 1 in which R$_1$ and R$_2$ are both SO$_3$M.

5. The compound of claim 1 in which R$_1$ is SO$_3$M and R$_2$ is COOM.

6. The compound of claim 1 in which R$_1$ is COOM and R$_2$ is SO$_3$M.

7. The process of claim 2 in which R$_1$ and R$_2$ are both SO$_3$M.

8. The process of claim 2 in which R$_1$ is SO$_3$M and R$_2$ is COOM.

9. The process of claim 2 in which R$_1$ is COOM and R$_2$ is SO$_3$M.

10. The process of claim 3 in which R$_1$ and R$_2$ are both SO$_3$M.

11. The process of claim 3 in which R$_1$ is SO$_3$M and R$_2$ is COOM.

12. The process of claim 3 in which R$_1$ is COOM and R$_2$ is SO$_3$M.

13. The process of using a compound as an inert fluorescent tracer in an industrial water system, wherein said compound is a compound of formula:

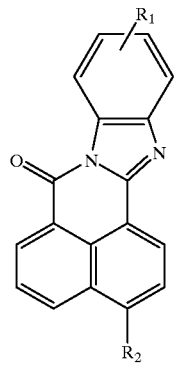

I wherein R$_1$ and R$_2$ are either both SO$_3$M, or one of R$_1$ and R$_2$ is SO$_3$M and the other is COOM, where M is selected from the group consisting of H, Na, K, Rb, Cs, Li or ammonium, the process comprising the steps of:
 a) providing an industrial water system,
 b) adding an amount of a compound of formula I to said industrial water system such that the system concentration of said compound of formula I is at least about 0.01 ppb and not more than about 10 ppm;
 c) providing a fluorometer capable of providing an excitation light in the range of 385–400 nm and capable of detecting an emission light in the range of 510–530 nm;
 d) using said fluorometer to detect the fluorescent signal of said compound of formula I in the industrial water system; and
 e) correlating said fluorescent signal of said compound of formula I to the amount of said compound of formula I present and relating the amount of compound of formula I present, to the hydraulic losses and gains in an industrial water system.

14. The process of claim 12 in which R$_1$ and R$_2$ are both SO$_3$M.

15. The process of claim 13 in which R$_1$ is SO$_3$M and R$_2$ is COOM.

16. The process of claim 13 in which R$_1$ is COOM and R$_2$ is SO$_3$M.

\* \* \* \* \*